United States Patent
Bruno et al.

(10) Patent No.: US 7,147,859 B2
(45) Date of Patent: Dec. 12, 2006

(54) APPLICATION OF PHYTOSTEROLS (AND THEIR ISOMERS), FOLIC ACID, CYANOCOBALAMIN AND PYRIDOXIN IN DIETETIC (ALIMENTARY) FIBERS

(75) Inventors: Roberto Luis Bruno, Sao Paulo (BR); Marcio Falci, Sao Paulo (BR)

(73) Assignee: Laboratorios Biosintetica LTDA., Taboao Da Serra (BR)

( * ) Notice: Subject to any disclaimer, the term of this patent is extended or adjusted under 35 U.S.C. 154(b) by 319 days.

(21) Appl. No.: 10/165,896

(22) Filed: Jun. 10, 2002

(65) Prior Publication Data
US 2003/0133965 A1    Jul. 17, 2003

Related U.S. Application Data

(63) Continuation-in-part of application No. 09/854,859, filed on May 14, 2001, now abandoned.

(30) Foreign Application Priority Data

May 15, 2000  (BR) .................................... 0001794

(51) Int. Cl.
*A61K 39/385*  (2006.01)
*A61K 47/00*  (2006.01)
*A61K 31/554*  (2006.01)

(52) U.S. Cl. ................... 424/195.1; 424/439; 424/464; 424/489; 514/211.02

(58) Field of Classification Search ............ 424/195.1, 424/439, 464, 489; 514/211.02
See application file for complete search history.

(56) References Cited

U.S. PATENT DOCUMENTS 5,132,113 A * 7/1992 Luca ........................... 424/750
5,700,782 A * 12/1997 Cope et al. ................... 514/21
5,770,217 A    6/1998 Kutilek, III et al.
5,770,749 A    6/1998 Kutney et al.
5,929,062 A    7/1999 Haines
5,932,562 A    8/1999 Ostlund, Jr.
5,985,300 A * 11/1999 Crotty et al. ............... 424/402
6,020,139 A *  2/2000 Schwartz et al. ............ 435/7.1
6,054,128 A *  4/2000 Wakat ......................... 424/765
6,126,943 A * 10/2000 Cheruvanky et al. ....... 424/750
6,139,872 A * 10/2000 Walsh ......................... 424/464
6,241,996 B1 * 6/2001 Hahn .......................... 424/439
6,251,878 B1 * 6/2001 Strickland et al. ............ 514/54
6,350,784 B1 * 2/2002 Squires ....................... 514/642
6,471,981 B1 * 10/2002 Hahn .......................... 424/439
6,716,462 B1 * 4/2004 Prosise et al. ................. 426/72
6,720,015 B1 * 4/2004 Prosise et al. ................. 426/72
2001/0031744 A1 * 10/2001 Kosbab ........................ 514/54

* cited by examiner

*Primary Examiner*—Vickie Kim
(74) *Attorney, Agent, or Firm*—Duane Morris LLP

(57) ABSTRACT

It relates to an Association of chemical agents, with intended pharmacological action to prevent the risk of infarction and brain hemorrhage caused by the development of the atherosclerotic process and of the homocysteinemia resulting from ageing.

It is of the utmost importance to prevent the increase of endogenous homocysteine.

High levels of homocysteine in blood, caused by genetical error and further biologic circumstances impart damaging consequences upon the human organism (occlusion of blood vessels, ocular modifications, osteoporosis and nervous system).

9 Claims, No Drawings

APPLICATION OF PHYTOSTEROLS (AND THEIR ISOMERS), FOLIC ACID, CYANOCOBALAMIN AND PYRIDOXIN IN DIETETIC (ALIMENTARY) FIBERS

CROSS-REFERENCE TO RELATED PATENT APPLICATIONS

This patent application is a continuation-in-part patent application of U.S. patent application Ser. No. 09/854,859, filed May 14, 2001 now abandoned, which is hereby incorporated in its entirety.

The present invention is related to a pharmaceutical dosage formula containing fibres, phytosterols, folic acid, B6 and B12 vitamins for the treatment and prophylaxis of hypercholesteremia and hyperhomocystinemia.

Hypercholesteremia is a well defined risk factor for the development of atherosclerotic disease, as well as for one of its more important complications, coronary insufficiency. In the same way, the biological properties and the cholesterol metabolism are well defined. This molecule is originated whether in the diet or through cellular synthesis, being part of cells normal structure, as well as functioning as a forerunner for the synthesis of steroids hormones. From the liver, it is taken to the organism cells through the LDL fraction of the blood lipoproteins. After the normal body cytolysis process, it is taken back to the liver by the HDL in order to be excreted together with the bile. Of this excreted cholesterol, approximately 60% will be reabsorbed by the small intestine, returning to the liver through the digestive system, ⅔ come from this source and the rest comes from diet sources. Hypercholesteremia is a result of the unbalance caused by dysfunction of one of these points of metabolic processing, depending on the subtype of dyslipidemy. Occasionally, the cholesterol will accumulate itself pathologically on the vascular subendothelium, thus causing the formation of the atheromatous plate.

Coronary insufficiency is the main cause of death in the western world. In 1996 in the USA, 41% of all deaths were caused by cardiovascular disease, and those with coronary nature prevailed. In the USA, it is considered that the majority of deaths due to coronary disease affects individuals with total serumal cholesterol of about 180 and 250 mg/dl. In some studies, it was shown that a 10% decrease in the total cholesterol levels would result in a 22% decrease in the coronary heart disease incidence. One of the ways to control the ingestion of cholesterol is set forth by the documents of NCEP (National Cholesterol Education Program).

In Brazil, the statistical data are not that rich, however, Duncan and colleagues have shown that in a population of Porto Alegre with an average cholesterol level of 202 mg/dl, 14.9% of it had cholesterol above 250 mg/dl. Nicolau and colleagues have shown that 16% of the individuals of a population in Sao Jose do Rio Preto presented total cholesterol above 240 mg/dl.

Methionine abnormal metabolism has been related to cardiovascular diseases for more than 20 years, and it was the first study of controlled cases with patients that suffers arterial/coronary diseases, and documented by angiography, published in 1976. Since then, several researches have studied the relation of homocysteine high levels as a factor of potential risk for cardiovascular diseases. The identification of individuals with high risk of developing coronary heart diseases can reduce the mortality related to myocardium infarct and other heart related diseases.

Homocysteine changes the activities of the vascular endothelium and the smooth muscle cells in a way that may cause cardiovascular disease or its advancing.

Laboratory studies have shown the different effects of homocysteine in the cardiovascular cells: homocysteine can induce the conversion of the phenotype of endothelial cells from anticoagulant to procoagulant, modify the cell cycle, affect the cellular function, and stimulate the cytokinesis production.

The liver usually contains all the complement of metabolising enzymes of homocysteine, however, in the case the hepatic metabolism is weakened, the liver cells will expel the homocysteine in the general circulation in order to be metabolised by cells of other tissues with the intention of diminishing the intracellular concentrations.

However, the homocysteine metabolism is limited in other organs and tissues, including vascular cells. Studies with cellular cultures have shown that the homocysteine intracellular concentrations in the vascular endothelium and other vascular cells are not kept by the metabolic route found in the liver. These cells do not express the CBS, the first enzyme of the stage of transsulphurisation, and do not express the betaine enzyme either; the homocysteine methyltransferase (BHMT), which catalyses the alternative route of remethylation in the liver, using betaine as substratum. The homocysteine metabolism is limited by the remethylation, which depends on $B_{12}$ vitamin and folate, catalysed by synthesis methionine. Vascular cells, in particular endothelial cells, can be especially vulnerable to high levels of circulating homocysteine found in patients with hypercholesteremia.

The association between the levels of homocysteine and conventional risk factors for vascular diseases may be extremely important to manage the risk and to understand vascular diseases. Whether in men or in women, an homocysteine high plasmatic level, in fasting situations, presents an independent risk of vascular diseases similar to those found in smokers or in individuals with high levels of cholesterol.

However, for both sexes, a high level of homocysteine, in fasting situations, has shown a higher multiplicative effect of cardiovascular diseases than those found in smokers or individuals that suffer hypertension.

Sterols

STEROLS are composites found in all natural fats and oils (animal and vegetal); it is stated, however, that during their industrial refining procedure, STEROLS are taken away and only a very small part is kept in the oil or fat destined to human consumption. Part of the STEROLS is taken away during the following refining phases: alkaline neutralisation, clarification and deodorisation. STEROLS are used in the manufacture of soap or, after their isolation and purification, they are reused as raw material for the manufacture of D vitamin and hormones.

Constitution:

STEROLS are secondary alcohols belonging to the steroids group. Vegetal oils STEROLS are collectively known as PHYTOSTEROLS. STEROLS are acyclic substances that contain the cyclopentanoperhydro phenanthrene nucleus.

| Natural Sterols | | |
|---|---|---|
| | | Molecular Weight |
| Zosterols (animal origin) | | |
| Cholesterol | $C_{27}H_{46}O$ | 386.64 |
| 7 Dehydrocholesterol | $C_{27}H_{44}O$ | 384.62 |
| Coprosterol | $C_{27}H_{48}O$ | 388.65 |
| Phytosterols: | | |
| Ergosterol | $C_{28}H_{44}O$ | 396.63 |
| Stigmasterol | $C_{29}H_{48}O$ | 412.67 |
| Betasitosterol | $C_{29}H_{50}O$ | 414.69 |
| Campesterol | $C_{28}H_{48}O$ | 400, 66 |
| Betasitostanol | $C_{29}H_{55}O$ | 416, 71 |

Phytosterols (and their isomers) are, therefore, an integral part of the formula of the present invention, since they present hypocholesteremic activities.

Phytosterols

Structural Formula

Ergosterol: $C_{28}H_{440}O$—Molecular Weight 396.63

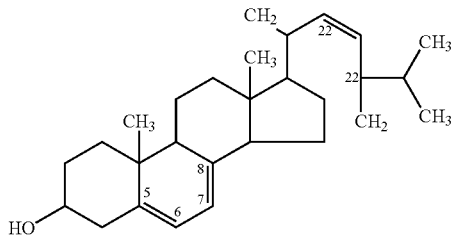

It is different from Stigmasterol by a methyl group in a lateral chain and two joint linkages in the positions 5:6 and 7:8.

Stigmasterol: $C_{29}H_{48}O$—Molecular Weight 412.67

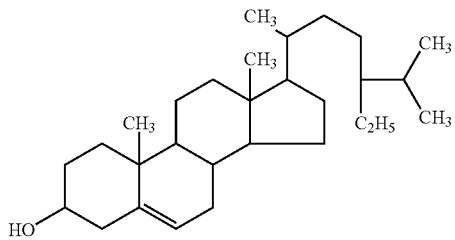

Betasitosterol: $C_{29}H_{50}O$—Molecular Weight 414.69

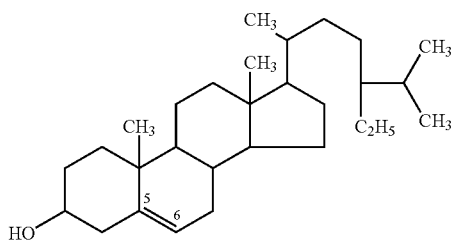

Campesterol: $C_{28}H_{48}O$—Molecular Weight 400.66

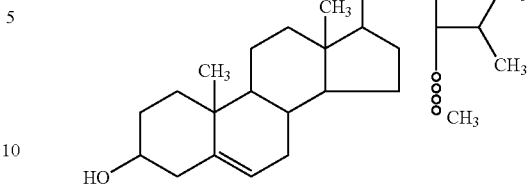

It is different from Betasitosterol, for having a methyl group instead of an ethyl, as a substitute in the lateral chain and from Ergosterol chain, because it does not have double linkage in the chain 7:8.

Betasitostanol: $C_{29}H_{52}O$—Molecular Weight 416.71

(Stigmastanol) Dehydro-β-Sitostanol

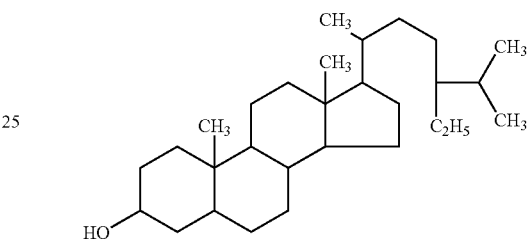

It has the same structure as Betasitosterol, but has a completely saturated chain. PHYTOSTEROLS and the major isomers thereof-Ergosterol, Stigmasterol, Betasitosterol, Betasitostanol, will be used in the crystallized, oily, alcoholic, aqueous, alginates (algae and its byproducts) and mucilaginous forms, with the purpose of conferring the desired effect, according to the prescription identified.

PHYTOSTEROLS—Biochemical Behaviour

Biostatics, configured in the behaviour of STEROLS in human organism, reveals, although not sufficiently, that the complexity involved in each phase of the reaction requires the presence of different bacterian agents, salts, vitamines, enzymes, minerals and catalysers to satisfactorily complete the biological-physiological cycle. These basic concepts have become elementary for configuring the planning of the hypocholesteremising action of sterols in order to achieve results evidencing efficiency in the reduction, under control, of cholesterol in entero-hepatic circulation. Biodynamics may point out quite precisely the participation of STEROLS, particularly Betasitosterol and Betasitostanol, incorporated to (ALIMENTARY) DIETETIC FIBER, through the use of radioactive isotopes, following the transformations occured in the organism and the secretions thereof. With this exposition of motives-biochemical behaviour-, we have sought to demonstrate that a traditional stoichiometric reaction cannot prevail to reveal the evidencing chemical reactions that prove the action of sterols.

The action of PHYTOSTEROLS is connected to the metabolism of lipids. PHYTOSTEROLS by oral dosage are practically not absorbed by the human intestines. Its cholesterolemising action is attributed to its great similarity to cholesterol, since its molecules link with the intestinal micelles. Therefore, the cholesterol molecules are not absorbed. The result thereof is the corresponding reduction of chylomicrons. Cholesterol reduction in hepatic contents concurs with the stimulus to capture LDL and produce less VLDL and apo B. PHYTOSTEROLS reduce hipercholesteremia systematically. PHYTOSTEROLS are derived from vegetal oils, thus being of natural origin and exempt of any side-effects related for hipocholesteremia-inducing drugs. The application of PHYTOSTEROLS by oral dosage does not require any effort for creating a habit of consumption, since they do not present any type of intolerance and do not require any adjustment of taste.

PHYTOSTEROLS, at intestinal level, link with cholesterol (zoosterols) and produce non absorbable micelles, thus providing a high degree of deactivation of the harmful effects caused by cholesterol (zoosterols) upon the human health.

Approximately 80% of sterols ingested coming from plants are betasitosterol. Therefore, this is the most common phytosterol in diet, and the phytosterol which is preferred to be used in its invention.

Initially, betasitosterol was given as a liquid suspension, in granules or in powder, at 10 to 15 g/day, which resulted in the reduction of cholesterol levels by 10% to 15% in relation to the initial basal levels.

Betasitosterol is absorbed by 2% to 5% of the ingested amount. Such ratio varies if it is ingested together with the diet (less absorbance) or isolatedly (more absorbance). Such absorbance is directly related to the lenght of its side chain. Betasitosterol can reduce cholesterol absorbance by up to 68%. The industrial process of transesterification does not affect its absorbance potential.

After absorbance, approximately 27% of betasitosterol is made up of glucuronate, cholic acid and chenodeoxycholic acid. Its half-life varies from 5.4 to 13.8 days.

Because of their structural similarity, betasitosterol can compete with cholesterol due to its incorporation to mixed intestine mycelia, and it it can be solved in mycelia three times as much as cholesterol itself. These mycelia are necessary to solubilise cholesterol in the bolus to be carried to the intestine mucosa. Since betasitosterol has a very low absorbance capacity in comparison to cholesterol (2% to 5% of betasitosterol against 40% to 60% of cholesterol), it will be mostly eliminated in feces together with a significant part of cholesterol, the absorbance of which it would have avoided.

The reduction in cholesterol absorbance will be followed by a compensatory increase in its hepatic synthesis. Nevertheless, the tendency of a new increase in cholesterol level will be compensated by an increase in hepatic receivers to LDL, and the net effect will be the reduction of total cholesterol and LDL cholesterol levels.

Betasitosterol does not affect HDL cholesterol and triglycerides levels. However, an increase in HDL cholesterol levels has been reported from a group of diabetic patients type II carrying mild hypercholesterolemia.

| ZOOSTEROLS (structural formula) | | |
|---|---|---|
| Cholesterol: | $C_{27}H_{46}O$ | mol. weight 386.64 |

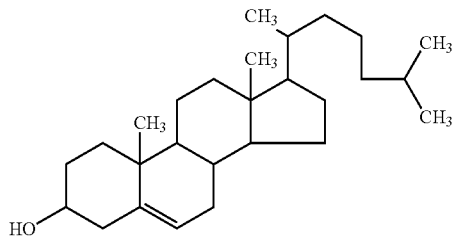

| ZOOSTEROLS (structural formula) | | |
|---|---|---|
| 7-Dehydrocolesterol: | $C_{27}H_{46}O$ | mol. weight 384.62 |

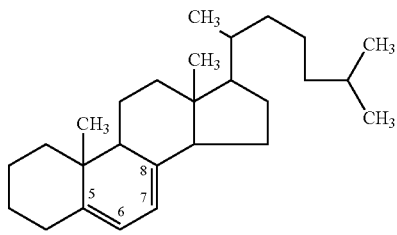

7-Dehydrocholesterol can be found, in small amounts, together with cholesterol in almost every animal tissue. It differs from cholesterol by having a double link between carbons 7 and 8. When radiated by ultraviolet light, it becomes D3 vitamin (anti-rachitic).

| Coprosterol: | $C_{27}H_{48}O$ | mol. weight 388.65 |
|---|---|---|

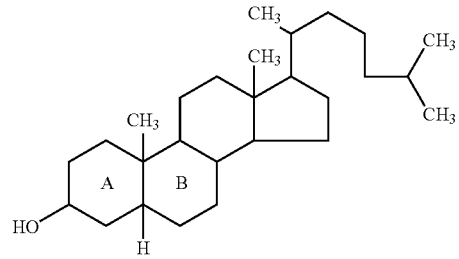

Coprosterol can be found in feces and is the final product obtained by cholesterol reduction in the intestinal tract (or by the action of intestinal bacteria). Its reduction enables the deleting of the double link, the union of A/B cycles thereof is of cis configuration. It must be taken into account that many individuals whose cholesterol levels are over 240 mg/dl do not present any defects of genetical nature. Therefore, this value may be attributed to anomalies resulting from alimentary issues.

Hyperhomocysteinemia, which is one of the factors that determine the risk of cardiovascular diseases, is related to a defect of genetical nature in the metabolism of CBS depending on PLP or on the enzymes involved in the metabolism of folates and B6 and B12 vitamines. This invention proposes the use of folic acid, B6 vitamin and B12 vitamin in the reduction of homocysteine levels in pacients carrying cardiovascular diseases.

FOLIC ACID $C_{19}H_{19}N_7O_6$ - Mol. Weight 441.40

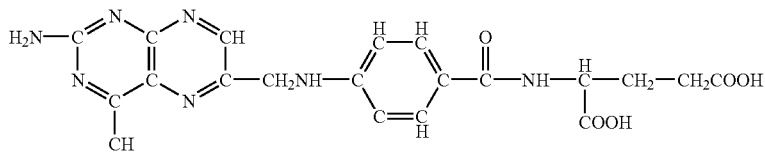

Folic acid intervenes in the biosynthesis of purines and thiamine. It participates in various processes, such as the growth process, particularly, in erytropoiesis. It can be found in the liver, kidneys, yeasts, milk, eggs, vegetal seeds and foliage. Its name, Folic, is derived from foliage. Folic acid (folacin, pteroylglutamic acid) is a composite of p-aminobenzoic acid and glutamic acid with pteridine nucleus.

Many researchers took part in its discovery and, due to the different techniques these researchers employed, resulted some factors identified by different names: vitamine M, U factor, R and S factors, norite eluate factor and streptococus lactis factor (SLR).

Folic acid takes part in the synthesis of the methyl (—CH3) group in the processes of homocystheine methylation for producing Methionine.

Methionine is indispensable in the diet; it keeps the nitrogenised balance for growth and life. Lack of methionine interrupts growth, causes multiple problems and may lead to death.

Folic acid, vitamine B6 and vitamine B12 take part in the organic synthesis of Methionine.

Another significant factor is the capacity of regenerating tetrahydrofolic acid starting from N5-methyltetrahydrofolic acid, which is the reduced form of folic acid, a self-regenerating catalytic composite that takes part in the transfer of carbon.

Folic acid is known to be present in various vegetal foods. Nevertheless, our organic reserves are very small, and mammals cannot synthetise it. Therefore, the deficit of folic acid causes the reduction of thiamine synthesis. This element participates in the formation of DNA, and not RNA.

Histidine also has its catabolism compromised; notwithstanding its clinical significance, it accumulates large quantities of the forminoglutamic acid metabolites (FIGLU).

B12 Vitamin

Cyanocobalamin $C_{63}H_{88}O_{14}N_{14}PCo$—Mol. Weight 1.355,4

B12 vitamin presents a complex structure for its composites, the best known of which is cyanocobalamin. It is found in animal products and as the result of the metabolism of microorganisms.

B12 vitamin participates in the metabolism of the methyl-labile Group, particularly in the biosynthesis of Methionine, by the transformation of Homocysteine and Choline through the participation of ethanolamine.

B 12 vitamin and folic acid (pteroylmonoglutamic acid) participate in a general way in the metabolism involving the synthesis and molecular interrelation of purines.

B12 vitamin cannot be synthetised in the human organism. The normal deposits in men come from alimentary ingestion; this is the reason why alimentary suplementation is necessary.

There are few metabolic reactions which are surely dependent on B 12 vitamin. The reactions of CoA methylmalonil are sufficiently clear, and they act in the isomeric conversion between CoA methylmalonil and CoA Succinil and, particularly, Homocysteine methylation to Methionine. This reaction produces Methionine and Tetrahydrofolate.

When the procedure of Homocysteine methylation does not occur perfectly, a relative deficit of Methionine results thereof.

The conversion of methylmalonate-succinate participates in the interconversion cycles of lipids and carbohydrates.

Studies performed in chicks and mice, administering homocysteine without the substances that provide the methyl (—CH3) group, such as methionine, betaine abnd choline, have shown the occurrence of disruption of the growth process of the animals.

Through the supplementation of liver extract or B12 vitamin, the corresponding growth was resumed. Therefore it has been evidenced that B12 vitamin participates in the methylation of homocysteine.

There are other cobalamines with properties of B12 vitamin activity:

| | |
|---|---|
| Hydroxicobalamin | B12b vitamin |
| Anhydrous form of the latter | B12a vitamin |
| Nitrocobalamin | B12c vitamin |

B12 Vitamin (Sources)

To obtain 1 g of B12 Vitamin of natural origin, more specifically of animal origin, 4 tons of bovine liver are required, rendering such obtaining unfeasible due to the high final cost of the product.

Having been verified that intestinal microorganisms synthesize B12 Vitamin, the procedures of industrial production were established based on a fermentation process by Streptomyces griseus (the same that produces streptomicin).

The concentration thereof, both in the fermenting liquid and in the liver is of one part per million (1 p.p.m.)

B6 Vitamin pyridoxin $C_8H_{11}O_3N.HCl$ (Pyridoxine Hydrochloride) Mol. Weight 205.6

B6 Vitamin is presented with three active components, and is characterized by the functional group in position 4, i.e. one pyridoxine alcohol (pyridoxol), one aldehyde (pyridoxal) and one amine (pyridoxamine). These three components (composed) are jointly designated as pyridoxine.

The pyridoxin aldehyde (pyridoxal) and pyridoxamine also have a vitaminic activity, being designated as the vitamins of the pyridoxine group. In the tissues, it is normally esterified with phosphoric acid, and combined with proteins of enzymatic nature.

Pyridoxal phosphate appears as the coenzyme of the transaminase enzymes.

Transamination in the human organism has its importance in the participation of deamination of amino acids by the transference of the amina group to α-ketoglutaric acid and the corresponding formation of glutamic acid.

The industrial and commercial product of B6 vitamin is alcohol hydrochloride (pyridoxine hydrochloride). Thus, 1 mg of pyridoxine hydrochloride corresponds to:

0.82 mg of pyridoxine (pyridoxol)
0.81 mg of pyridoxal
0.82 mg of pyridoxamine

As pyridoxal-5-phosphate, B6 vitamin acts as coenzyme of ferments that catalyze the transamination, deamination, decarboxylation, desulphydration and several divisions or syntheses of amino acids.

Deamination and desulphydration are related to the catabolism and anabolism of amino acidos, particularly in the liver.

The normal metabolism of amino acids is of great importance to the disintoxication reactions, with the corresponding elimination of substances harmful to the human organism.

B6 vitamin also takes part in the maintenance of a proper level of CoA in the liver. The metabolism of fatty acids becomes reduced in the absence of B6 vitamin, resulting in problems with the metabolism of lipids.

In the metabolism of cysteine, the B6 vitamin reactions are related to the transference of sulfur from metionine to serine, resulting in cysteine. Therefore B6 vitamin is related to transamination and trans-sulfuration. The corresponding removal of sulfur from cysteine or homocysteine has the participation of desulphydrases, with the help of pyridoxal phosphate as coenzyme.

Thus B6 vitamin plays different roles in thee metabolism of amino acids:

As coenzyme for the decarboxylation and deamination of serine and treonine
In the transamination, trans-sulfuration and desulfuration of cysteine and homocysteine.
In the transference of amino acids to the interior of cells.

Dietetic Fibers (Alimentary)

The use of dietetic fibers (alimentary) in human feeding is consolidated in the more knowledgeable urban societies, just like several other products, as occurred as of the decade of the twenties with refined sugar.

The dietetic fibers (alimentary) correspond to the organic residues of foodstuff (animal or vegetal) that cannot be hydrolized by the human digestive juices. The dietetic fibers (alimentary) with the purpose of contributing to better health are presented in the domestic market under the commercial denomination of, for instance, Müsli, All Bran, Fibrex. Such fibers may be ingested under the form of, for instance, cereal flakes, biscuits, grain bran in general (from grains of wheat, oats, barley, rye, plantain etc.) and mucilages. Other products presented in the form fibers are those resulting from the autolyses of animal products and the residues from the extraction of sugar from sugar beets.

The major components of dietetic fibers are the structured substances that exist in the cellular walls of vegetables: cellulose, hemicellulose, pectin and lignin, as well as non-structured polysaccharides (gums, mucilages and algae polysaccharides) also present in the cellular cytoplasm.

Chemically, cellulose consists of linear D-glucose polymers, linked by β1–4 glucosidic bridges. Therefore, cellulose is a linear polymer of glucose (carbohydrate) having a mollecular weight ranging from 60,000 to 20,000,000. The main function of cellulose in the intestines is to link with water, one of its grams being capable of retaining 400mg of water.

Hemicellulose

Hemicellulose consists of homo or heteropolysaccharide complexes, of high mollecular weight. The polymer presents from 150 to 250 units of mannose. Hemicellulose can be of two types:

Hemicellullose A containing residues of:
xylose
galactose
mannose
arabinose
glucose Hemicellullose B (Acid) Containing Residues of:
uronic acids (galactouronic and glucouronic)

Like cellulose, hemicellulose is also a carbohydrate, comprising pentoses and hexoses, frequently branched. Its molecular weight varies from 10,000 to 20,000. At intestinal level, hemicellulose is capable of retaining water, and has the property of linking to cations.

Pectin

Pectin is found in the vegetal wall, linked to hemicellulose and intermeshed with cellulose fibers. Pectin and pectinic substances consist of a coloidal combination of polysaccharides derived from galacturonic acid polymers with chains of pentose and hexose, having a molecular weight of about 60,000 to 90,000. It produces gel by retaining water, and links to cations and organic matter, promoting the excretion of biliary acids.

Lignin

Lignin is a polymer having a molecular weight from 1,000 to 10,000, made of units of phenyl-propane linked by carbon-carbon connections and is not a carbohydrate. In the treatment of problems involving the intestines, it represents an inhibitor of microbial digestion of the cellular walls, since it coats cellulose and hemicellulose, and may inhibit the division of carbohydrates of the cellular walls. Lignin is capable of combining with biliary acids, forming non-absorbable complexes (unsoluble), reducing the cholate levels in blood and providing the transformation of hepatic cholesterol into biliary salts.

Non-structured polysaccharides (gums, mucilages and algae polysaccharides) also present in the cellular cytoplasm Gums Gums are vegetal (plant) exsudates having as primary units: galactose, glucouronic acid, mannose, galactouronic acid Mucilages Mucilages are the product of current metabolism of vegetals, having as primary units: galactose, mannose, glucose, mannose arabinose, xylose and galactouronic acid.

Gums and mucilages represent a complex of non-structured polysaccharides, and may form gel in the small intestine, and link with biliary acids and other organic matter. They promote the increase of volume of the fecal bolus, and participate in the reduction of cholesterol by changing the metabolism of salts.

Algae Polysaccharides

Derived from primary units of mannose, xylose, glucouronic acid, they are complex polymers. The anaerobic fermentation of the polysaccharides results in energy for the development and preservation of the bacterial flora of the colon.

The microflora of the colon dehydroxilates biliary acids and hydrolizes glucouronic conjugates, and may even synthesize vitamins.

Biliary Acids

They have a cyclic structure derived from perhydrocyclopentanofenantrene, with a lateral chain of acid function, admitted as being derived from hydroxilates and colanic acid.

The spatial structure of the cycles corresponds to androstane, coprostane and hydroxil of lithocholic acid, to epicoprostanol

---

Cholanic acid $C_{24}H_{40}O_2$    mol. weight 360.56

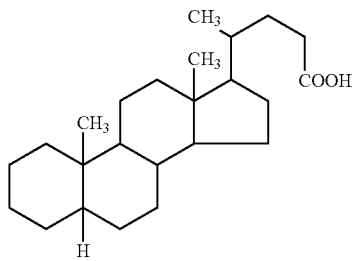

---

In human bile we find:

---

| lithocholic acid containing one alcohol hydroxil | $C_{24}H_{40}O_3$ |
| desoxycholic acid with two hydroxils | $C_{24}H_{40}O_4$ |
| anthropocholic acid (isomer of desoxycholic) | $C_{24}H_{40}O_4$ |
| cholic acid with three hydroxils | $C_{24}H_{40}O_5$ |

Others of lesser significance:

--- lithocholic acid    $C_{24}H_{40}O_3$    mol. weight 376.56

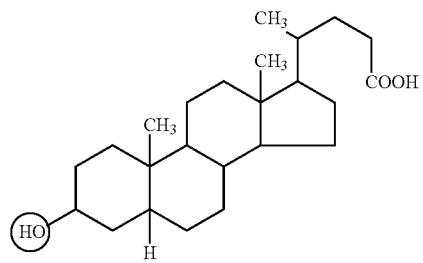

---

-continued desoxycholic acid    $C_{24}H_{40}O_4$    mol. weight 392.56

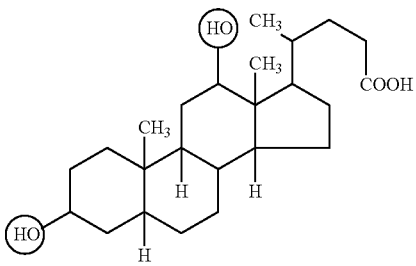

cholic acid    $C_{24}H_{40}O_5$    mol. weight 408.56

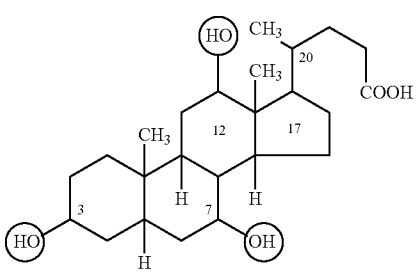

---

Note:
These acids are found in the bile in the form of salts, mostly sodic, and the others linked to glycocoll and taurine (peptide type) attached to the carboxyl of biliary acid (amina group of aminated acid).
$C_{23}H_{39}O_3.COOH + NH_2.CH_2—COOH \rightarrow C_{23}H_{39}O_3.CO—NH.CH_2—COOH$
Glycocholic acid is found in the bile as a sodium salt.

Cholic acid also reacts with taurine ($NH_2CH_2—CH_2SO_3H$) having as product taurocholic acid. Taurine is an amino acid derived from cysteine or from the oxidation of cystine.

---

$C_{23}H_{39}O_3.COOH + NH_2CH_2—CH_2SO_3H \rightarrow$
$\phantom{C_{23}H_{39}O_3.COOH + NH_2CH_2—CH_2SO_3H \rightarrow}C_{23}H_{39}O_3.CO—NH.CH_2—SO_3H$
cholic acid    taurine    taurocholic acid
taurocholic acid:    $C_{26}H_{45}NO_7S$    mol. weight 515.69

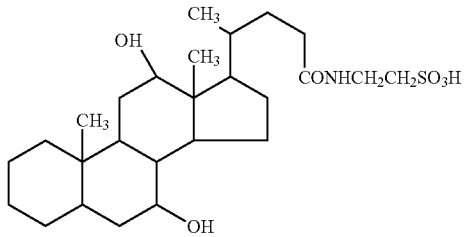

Further derivatives of cholic acid:

norcholanic acid    $C_{23}H_{38}O_2$    mol. weight 346.53
(obtained from ethylcholanote)

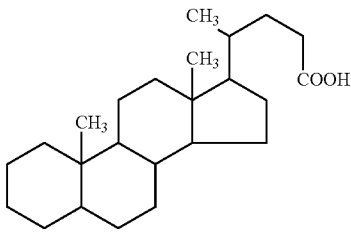

-continued ursodeoxycholic acid    C$_{24}$H$_{40}$O$_4$    mol. weight 392.56

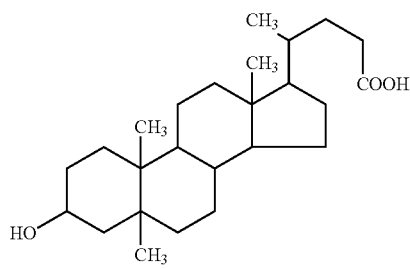

chenodeoxycholic acid    C$_{24}$H$_{40}$O$_4$    mol. weight 392.56
(component of bile)

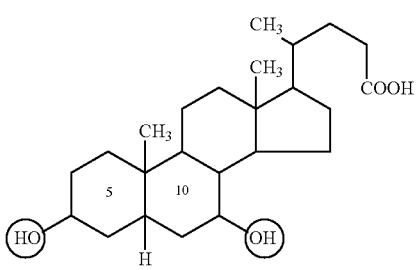

dehydrocolic acid: C$_{24}$H$_{34}$O$_5$ - Mol. Weight 402.51

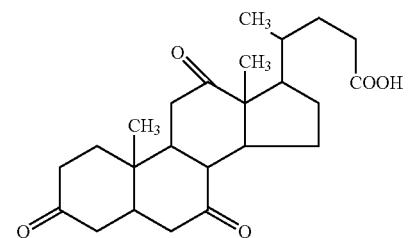

NOTE:
It is admitted that biliary acids are produced in the liver. This fact can be proved by the administration of tagged CHOLESTEROL (deuterium). It can be observed that part of it is oxidised, forming biliary acids. The direct synthesis of biliary salts and cholesterol must also be taken into account. Biliary salts are insoluble in water and soluble in alcohol. However, they reduce surface tension, and as surfactants they favour the dissolution of poorly soluble or insolublesubstances. Experimentally it may be seen that a solution of sodium deoxycholate increases the solubility in water of fatty acids, menthol and camphor.

Properties of great importance in the process of digestion and fat absorption.

One of the known fibers which is already marketed is beet fiber, which was developed by the Swedish company Danisco and bears the trademark Fibrex. Fibrex is beet pulp which is dehydrated through vapour heated under pressure. The final product is a light-coloured pulp which is processed in order to produce flakes or a ground product to be added to other types of foods.

The process of beet dehydration causes the vegetable's cells to collapse. When diet water is added to Fibrex again, these cells assume their original morphology, thus conferring the product a jelly consistency.

It is supposed that beet fiber, after it becomes a gel due to the contact with water, would acquire the property of adherence to biliary acids and cholesterol, thus increasing their elimination through feces.

Association of Phytosterols and (Alimentary) Dietetic Fibers.

Phytosterols (and isomers thereof) and polyunsaturated fatty acids incorporated to (alimentary) dietetic fibers will constitute a highly potentiated association of therapeutic contribution to a greater range of needs of application.

(Alimentary) dietetic fibers as excipient, with their physiological and medicamental action, dignify the association, providing the most ample spectrum of therapeutic contribution.

The positioning of the product of the association of phytosterols and (alimentary) dietetic fibers will be in the direction of Medicinal, non ethical Alimentary complement (natural)

The presentation may be in form of powder, dragées, capsules, pills, creams, different emulsions, emulsified granulate and concentrate. The detail of product presentation for prescriptive use is set forth according to therapeutic application or the habit of ingestion made easier. Both the form of the product and the amounts packed shall be pursuant to its specific use and its respective consumption contribution.

Thus, this invention corresponds to a formulation of pharmaceutical dosage containing dietary fiber, sitosterol, folic acid, B6 vitamin and B12 vitamin for the treatment and prophylaxis of hypercholesterolemia and hyperhomocysteinemia.

The following examples illustrate this invention, which refers to the formulation of the product based on fibers and folic acid, B6 and B12 vitamins.

EXAMPLE 1

| Each 100 g contains: | |
| --- | --- |
| Whole milk powdered | 4.200 g |
| Fibrax 608 | 26.100 g |
| Betasitosterol | 2.700 g |
| Oat flakes | 2.473 g |
| Rice crispies | 15.000 g |
| Folic acid | 0.0010 g |
| B6 vitamin | 0.025 g |
| B12 vitamin | 0.0005 g |
| Passion fruit pulp | 4.000 g |
| Orange flavour 5119/DP | 0.200 g |
| Fumaric acid CWS | 0.010 g |
| Salt | 0.010 g |
| Glucose syrup | 45.000 g |
| Liquid sugar | 10.000 g |
| Soy lecithin | 0.200 g |
| Cocoa fat | 3.000 g |

EXAMPLE 2

| Each 100 g contains: | |
| --- | --- |
| Whole milk powdered | 4.200 g |
| Fibrax 608 | 33.000 g |
| Betasitosterol | 3.600 g |
| Oat flakes | 0.001 g |
| Rice crispies | 9.700 g |
| Folic acid | 0.002 g |
| B6 vitamin | 0.050 g |

-continued

| Each 100 g contains: | |
|---|---|
| B12 vitamin | 0.001 g |
| Passion fruit pulp | 4.000 g |
| Orange flavour 5119/DP | 0.200 g |
| Fumaric acid CWS | 0.010 g |
| Salt | 0.010 g |
| Glucose syrup | 45.000 g |
| Liquid sugar | 10.000 g |
| Soy lecithin | 0.200 g |
| Cocoa fat | 3.000 g |

The objective of the formulation in example 2 is to serve as a treatment.

These preparations are in the form of a bar. A dry mixture of whole milk powdered, fibrex 608, betasitosterol, oat flakes, rice crispies, folic acid, B5 Vitamin, B12 Vitamin, passion fruit pulp, orange flavour 5119/DP, fumaric acid CWS and salt was added to a syrup previously prepared with glucose syrup, liquid sugar, soy lecithin and cocoa fat until it formed a homogeneous wet dough. This wet dough was pressed by adequate equipment and separated in 25 g bars.

The concentrations of the fibers, the folic acid and the B6 and B12 vitamins employed in the formulations according to what was demonstrated in examples 1 and 2 have the already scientifically proved activity which was previously described. The recommended dosage per day is one 25 g bar after the two main meals (lunch and dinner for the majority of people).

The formulations according to examples 1 and 2 in the form of powder, dragees, capsules, pills, creams, different emulsions, emulsified granulate and concentrate do not present any problem related to uniformity or coherence of the contents of active ingredients.

The invention claimed is:

1. An oral pharmaceutical formulation comprising phytosterols and isomers thereof, folic acid, cyanocobalamine, pyridoxine and dietetic alimentary fibers intended for the treatment and prophylaxis of hypercholesteremia and hyperhomocysteinemia, wherein said phytosterol is present in an amount of about 2.7% to about 3.6% by weight; said folic acid is present in an amount of about 0.001% to about 0.002% by weight; said cyanocobalamine is present in an amount of about 0.0005% to about 0.001% by weight; said pyridoxine is present in an amount of about 0.025% to about 0.05% by weight; and said dietary fiber is present in about 26.1% to about 33.0% by weight.

2. An oral composition for reducing hypercholesteremia and high blood homocysteine levels comprising an admixture of a phytosterol seleted from the group consisting of ergosterol, stigmasterol, betasitosterol, campesterol, betasitostanol, and isomers thereof; folic acid; cyanocobalamine; pyridoxine; and dietary fiber, wherein said phytosterol is present in an amount of about 2.7% to about 3.6% by weight; said folic acid is present in an amount of about 0.001% to about 0.002% by weight; said cyanocobalamine is present in an of about 0.0005% to about 0.001% by weight; said pyridoxine is present in an amout of about 0.025% to about 0.05% by weight; and said dietary fiber is present in about 26.1% to about 33.0% by weight.

3. The composition of claim 2, wherein said composition is a pharmaceutical composition formulated as a powder, a sugar-coated pill, a capsule, a tablet, a paste, an emulsion, or a granulate.

4. The composition of claim 2, wherein said dietary fiber is beet fiber.

5. The composition of claim 2, wherein said phytosterol is betasitosterol.

6. The composition of claim 2, wherein said composition is in the form of a bar.

7. The composition of claim 6, wherein said bar further comprises whole milk, oat flakes, rice crispies, fruit pulp, flavoring, fumaric acid, salt, glucose syrup, liquid sugar, soy lecithin and cocoa fat.

8. A method for reducing hypercholesteremia which comprises administering the composition of any one of claims 1, 2, 4, 5 or 6 to a subject for a time and in an amount to reduce cholesterol levels.

9. A method for reducing high blood homocysteine levels which comprises administering the composition of any one of claims 1, 2, 4, 5 or 6 to a subject for a time and in an amount to reduce homocysteine levels.

* * * * *